United States Patent

Wuchinich

[11] Patent Number: 5,300,021
[45] Date of Patent: Apr. 5, 1994

[54] APPARATUS FOR REMOVING CORES OF THERMOPLASTIC AND ELASTOMERIC MATERIAL

[75] Inventor: David G. Wuchinich, New York, N.Y.

[73] Assignee: SonoKinetics Group, Hoboken, N.J.

[21] Appl. No.: 932,786

[22] Filed: Aug. 20, 1992

[51] Int. Cl.$^5$ .............................................. A61B 17/20
[52] U.S. Cl. .................................. 604/22; 606/169; 606/99
[58] Field of Search ............ 128/24 AA, 912; 604/22, 604/905; 606/169-171

[56] References Cited

U.S. PATENT DOCUMENTS

| | | | |
|---|---|---|---|
| 4,184,510 | 1/1980 | Murry et al. | 604/22 |
| 4,195,440 | 4/1980 | Rodrigue | 604/22 |
| 4,248,232 | 2/1981 | Engelbrecht et al. | 606/169 |
| 4,516,398 | 5/1985 | Wuchinich | 604/22 |
| 4,921,476 | 5/1990 | Wuchinich | 604/22 |
| 5,019,083 | 5/1991 | Klapper et al. | 606/99 |
| 5,047,021 | 9/1991 | Utterberg | 604/905 |
| 5,131,382 | 7/1992 | Meyer | 604/22 |
| 5,151,083 | 9/1992 | Pichler | 128/24 AA |
| 5,154,696 | 10/1992 | Shearing | 604/22 |

FOREIGN PATENT DOCUMENTS 9107138  5/1991  World Int. Prop. O. ............ 604/22

Primary Examiner—C. Fred Rosenbaum
Assistant Examiner—Michael Rafa
Attorney, Agent, or Firm—R. Gale Rhodes, Jr.

[57] ABSTRACT

Apparatus including a receptacle mounted on the handpiece of ultrasonic apparatus which utilizes ultrasonic energy for removing cores of thermoplastic material such as bone cement used to implant prostheses. The receptacle is placed in fluid communication with an acoustical conductor extending through the apparatus and a tubular tip provided at the end of the conductor which tip is vibrated ultrasonically to remove the cores, for example of bone cement. The receptacle is connected to a source of suction, and the cores are drawn or aspirated through the tubular tip, the acoustical connector, and into the receptacle. A filter may be provided in the receptacle to assure that cores received in the receptacle are not drawn or aspirated out of the receptacle through flexible tubing which interconnects the receptacle to a source of suction.

25 Claims, 3 Drawing Sheets

APPARATUS FOR REMOVING CORES OF THERMOPLASTIC AND ELASTOMERIC MATERIAL

BACKGROUND OF THE INVENTION

This invention relates generally to new and improved apparatus, and components thereof, for removing cores of thermoplastic and elastomeric material.

Surgical aspiration is a well established medical technique for clearing operative sites of biological fluids and tissue, enabling the surgeon to obtain a clear view of the procedure. An enhancement to surgical aspiration, known as ultrasonic surgical aspiration, has been developed within the last twenty years to make possible direct aspiration of soft tissues, without the need for separate dissecting instruments, in surgical procedures. This art is principally described by Banko (U.S. Pat. No. 3,589,363) and Wuchinich (U.S. Pat. Nos. 4,063,557; 4,223,676; 4,425,115; 4,493,694; 4,516,398; 4,750,902; 4,750,488).

More recently, the use of ultrasonic vibration to cut and remove methylmethacrylate bone cement has been described by Englebrecht (U.S. Pat. No. 4,248,232) and Klapper (U.S. Pat. No. 5,019,083). The inventor of the present invention extended the technique to actual simultaneous removal and aspiration of the removed bone cement, e.g. methylmethacrylate, a thermoplastic material. The extensions of this technique are disclosed in U.S. patent application Ser. No. 07/529,029, entitled "APPARATUS AND METHOD FOR REMOVAL OF CEMENT FROM BONE CAVITIES," filed May 25, 1990 and U.S. patent application Ser. No. 07/439,114, entitled "ENDOSCOPIC ULTRASONIC ROTARY ELECTROCAUTERIZING ASPIRATOR," filed Nov. 17, 1989; the first figure of these applications is FIG. 1 of the present drawings. More particularly, it will be understood that the present invention is an improvement of the apparatus shown in FIG. 1.

Referring to FIG. 1, a femur 1 is shown following removal of the prosthetic implant 3. A cavity 4 remains whose walls are lined with bone cement 2. This bone cement is excavated or removed by the ultrasonic apparatus 30 having a hollow ultrasonic tip 6 that vibrates in the directions indicated by arrow 15. The tip 6 is a tubular tip of acoustically conductive material mounted to and aligned with a longitudinally extending tubular ultrasonic conductor 18 of acoustically conductive material which conductor is mounted to the handpiece 17. Surrounding and acoustically coupled to the conductor 18 is an ultrasonic transducer 19 connected to an ultrasonic generator 21 by the transducer power cable 12. The rearward end of the conductor 18 is connected to a vacuum receptacle or canister 14 by flexible tubing 11 which tubing may be provided with an optional trap 13 of suitable porous or mesh material. The canister 14 may be connected to a suitable vacuum source 23 by other flexible tubing 24. In operation, the tubular tip 6 is vibrated at a suitable ultrasonic frequency and is applied to the rim of bone cement 2 and this application locally melts the bone cement 2 of the thermoplastic material which material is then drawn or aspirated into the tubular tip 6 by the suction applied to the rear end of the conductor 18 and applied through the conductor to the tubular tip 6. The melted cement recrystallizes within the tubular tip 6 into a solid sliver or core of bone cement or thermoplastic material and it will be understood that it is within this context that the expression "cores of material (e.g. thermoplastic material) are removed and inserted into the tip (or tube)" is used in this specification and in the appended claims. Then the core is drawn or aspirated through the connector 18, tubing 11 and into the canister or receptacle 14, or if present into the optional trap 13, by the suction from the source 23. This operation is repeated, and as it is repeated successive cores of removed bone cement are drawn or aspirated into either the trap 13 or receptacle 14 by the suction applied to the rear end of the conductor 18. The pathway of a removed cylindrical cores of recrystallized bone cement is illustrated by the cores identified by numerical designation 26 and shown in solid outline in FIG. 1. Typically, the canister or receptacle 14 is located on the floor of the operating room, and to provide the surgeon operating the handpiece 17 of the ultrasonic apparatus 30 with the maneuverability required for the removal of the bone cement 2 as described above, the flexible tubing 11 must be several feet in length. During maneuvering of the handpiece 17 of the ultrasonic apparatus 30, curvature is imparted to the flexible tubing 11, and since the removed cores of bone cement 26 are linear the possibility exists that the aspirated cores of bone cement 26 may lodge in such curvature and progressively develop into an obstruction or blockage in the tubing 11 as successive removed cores jam against one another in the curvature of the tubing. Without special provision for immediate, in-line collection of the removed cylindrical cores of bone cement, the acoustical surgical procedure of removing the bone cement 2, for example in hip joint revision arthoplasty, is or can be confounded by repeated loss of suction or aspiration and inordinate amounts of time spent clearing or freeing the suction passage through the tubing 11 from a blockage of removed bone cement cores 26. Such a blockage removal causes an interruption of the bone cement removal procedure which causes the patient to be on the life support system a longer amount of time than is desirable; it is generally believed that the longer the patient is on a life support system the greater the opportunity for an embolism to develop. Thus, the inherent safety and speediness of ultrasonic bone cement removal can be severely compromised by the extended amount of time taken to perform the surgical procedure, such as the noted hip joint revision arthoplasty, without the provision of apparatus which receives and collects the removed cylindrical cores of bone cement 26 in a manner which prevents the cores of removed bone cement from being jammed together in the suction or aspiration passageway, particularly flexible tubing such as tubing 11 of FIG. 1, thereby enabling uninterrupted and hence relatively quick use of the ultrasonic apparatus 30 by the surgeon in performing the required removal of the bone cement 2. Accordingly, there exists a need in this art for the provision of such bone cement receiving and collection apparatus.

SUMMARY OF THE INVENTION

It is the object of the present invention to satisfy the foregoing need in the art.

Apparatus satisfying this need may include a receptacle mounted on the handpiece of ultrasonic apparatus which utilizes ultrasonic energy for removing cores of thermoplastic material such as bone cement used to implant prostheses; the apparatus also may be used to remove cores of elastomeric material. The receptacle is placed in fluid communication with an acoustical conductor extending through the apparatus and a tubular tip provided at the end of the conductor and which tip is vibrated ultrasonically to remove the cores. The receptacle is connected to a source of suction, and the cores are drawn or aspirated through the tubular tip, the acoustical connector, and into the receptacle. A filter may be provided in the receptacle to assure that-cores received in the receptacle are not drawn or aspirated out of the receptacle and into flexible tubing which interconnects the receptacle to a source of suction.

The apparatus of the present invention further includes a receptacle for being mounted to ultrasonic apparatus for removing cores, for example, of bone cement. Still further, the present invention includes a connector for removably connecting such receptacle to such ultrasonic apparatus.

DESCRIPTION OF THE PREFERRED EMBODIMENT

Figure 1:
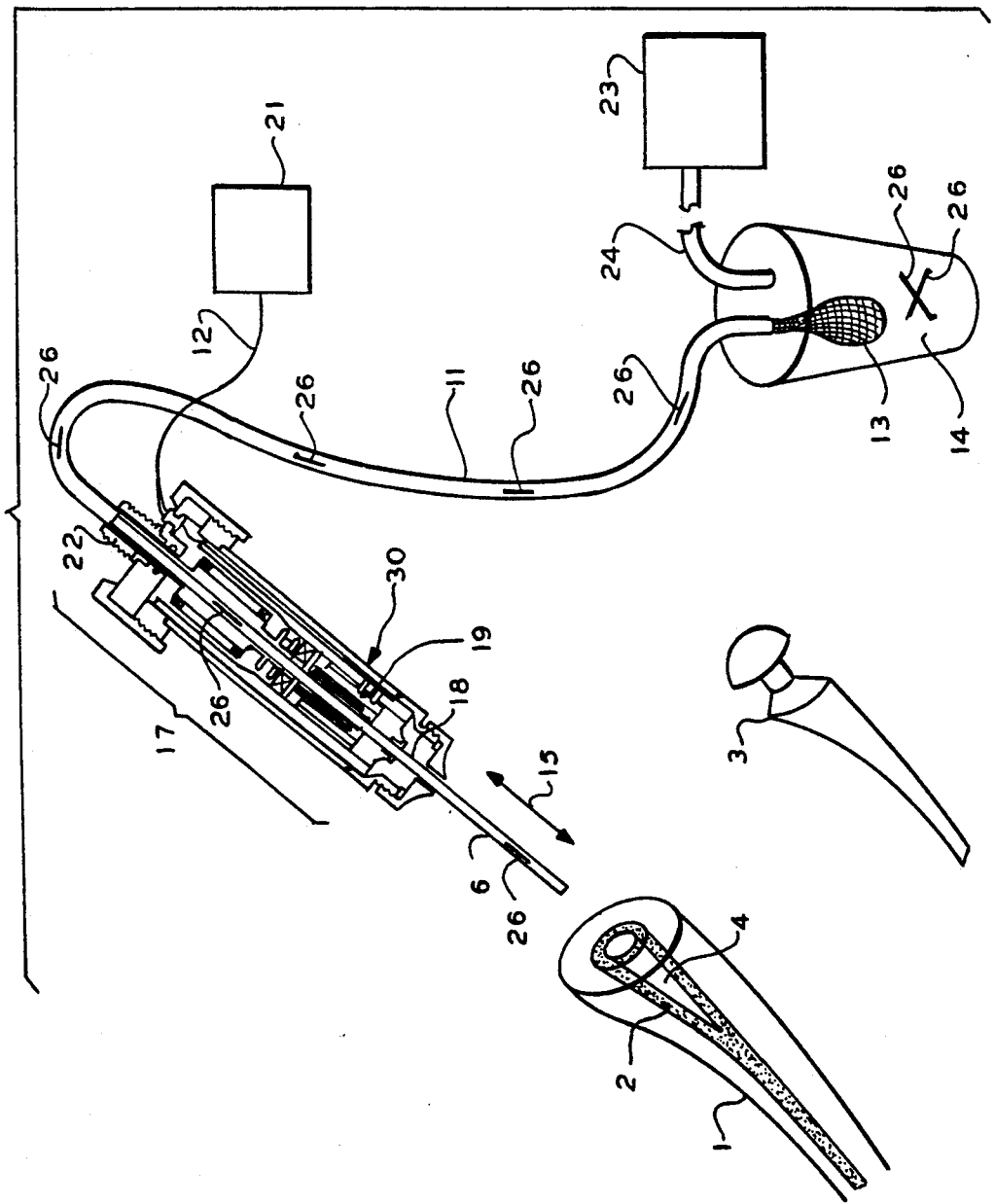
FIG. 1, as noted above, is the first figure in the United States patent applications referred to in the background of the invention.
Figure 2:
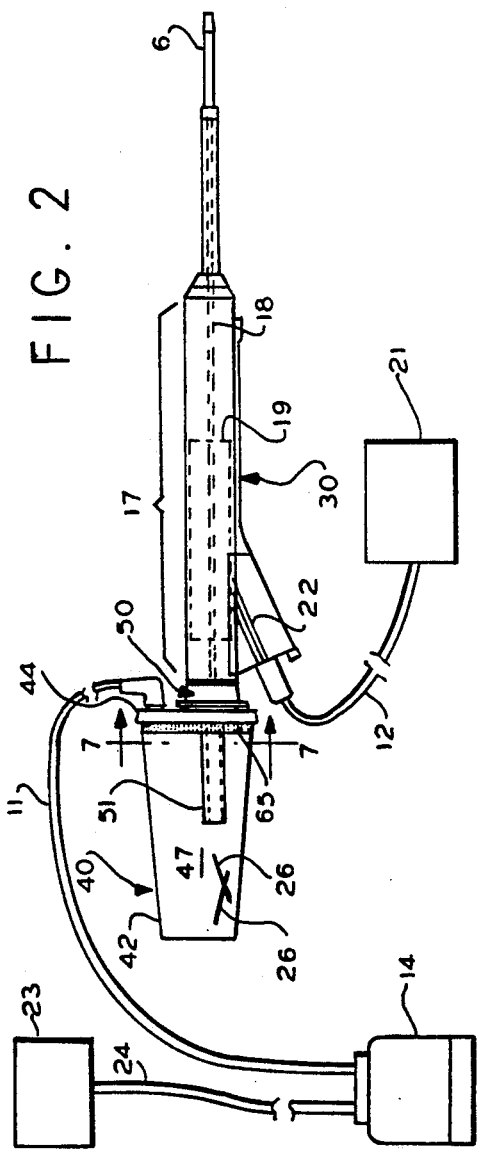
FIG. 2 is a diagrammatical illustration of apparatus of the present invention including in combination, ultrasonic apparatus including a handpiece for removing cores, for example of bone cement, a receptacle for receiving the cores and a connector for mounting the receptacle to the handpiece.

Referring now generally to FIG. 2, it will be understood that for convenience of presentation elements of the present invention shown in FIG. 2 which are the same, or substantially the same, as the elements shown in FIG. 1 and described above have been given the same numerical designations. In addition, the apparatus of the present invention includes a canister or receptacle indicated by general numerical designation 40 and a connector indicated by general numerical designation 50. It will be generally understood that the receptacle 40 unlike the receptacle 14 of FIG. 1 is mounted removably to the handpiece 17 of the ultrasonic apparatus 30 by the connector 50.

Figure 3:
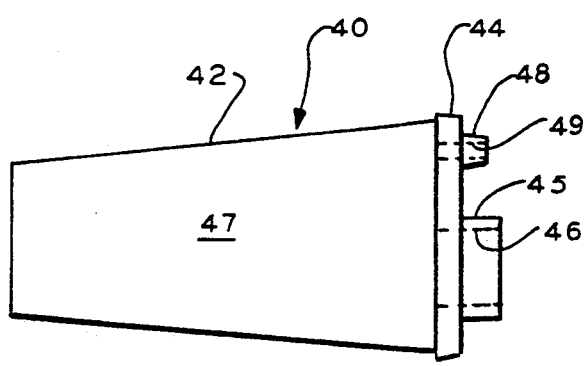
FIG. 3 is an enlarged side view of the receptacle shown in FIG. 2.

The canister or receptacle 40 is shown separately and in greater detail in FIG. 3. Receptacle 40 may include a generally truncated hollow conical body 42 which may be suitably molded from a suitable transparent plastic and a generally circular end cap 44 which also may be suitably molded from a suitable plastic. The end cap 44 is configured to removably engage and enclose the open rightward end portion of the body 42, the other end of which body 42 is closed, and the end cap may include an integrally formed tubular member 45 provided with an internal passageway 46 opening into and in fluid communication with the interior of the receptacle 40 which interior provides an internal cavity 47. In addition, the end cap 44 may be provided with an integrally formed tubular fitting 48 provided with an internal passageway 49 in fluid communication with the internal cavity 47 of the receptacle 40. As may be understood by reference to FIG. 2, the internal cavity 47 of the receptacle 40 is connected to the vacuum source 23 through the flexible tube 11 connected to the fitting 48, intermediate canister 14 which, in the apparatus of the present invention is used only for the receipt and collection of soft tissue and which is not used for the collection and receipt of cement bone cores 26, and the flexible tube 24.

Figure 4:
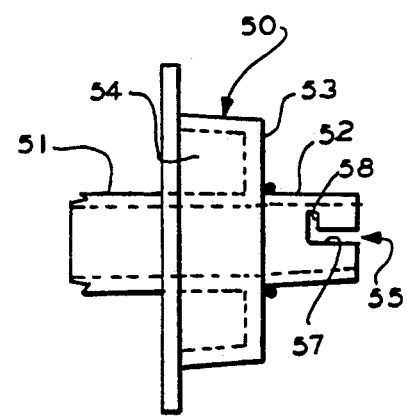
FIG. 4 is an enlarged side view of the connector shown in FIG. 2.
Figure 5:
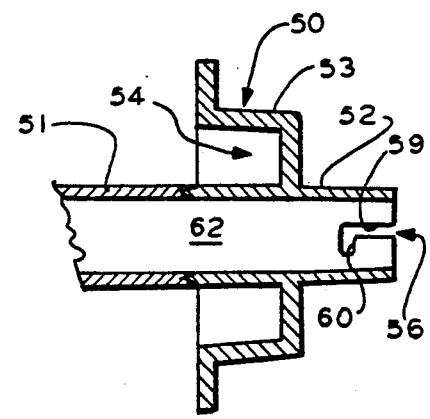
FIG. 5 is a vertical cross-sectional view of the connection shown in FIG. 4.

The connector 50 is shown separately, enlarged and in greater detail in FIG. 4 and may include a first tubular member 51, a second tubular member 52 which tubular members, as may be understood from the cross-sectional view shown in FIG. 5, may be formed integrally. The connector 50 may further include a radially outwardly extending cap 53 providing in combination with the tubular member 52 a generally annular recess 54 which is best seen in FIG. 5. The tubular member 52, FIGS. 4 and 5, is provided with a pair of opposed slots indicated respectively by general numerical designation 55 in FIG. 4 and general numerical designation 56 in FIG. 5. Slot 55, FIG. 4, includes an inwardly extending portion 57 and an upwardly extending portion 58, and slot 56, FIG. 5, includes an inwardly extending portion 59 and a downwardly extending portion 60. As may be further understood from FIG. 5, tubular members 51 and 52 cooperatively provide a passageway 62 extending through the connector 50.

It will be generally understood that the connector 50, FIGS. 4 and 5, is mounted removably to the receptacle 40 of FIG. 3. More particularly, the tubular member 51 provided on the connector 50 is provided with an external diameter which permits the tubular member 51 to be inserted into and through the internal passageway 46 provided in the tubular member 45 of the receptacle 40. The rightward end portion of the tubular member 45 of the receptacle 40 is inserted into the annular recess 54 provided in the connector 50 and such end portion is wedgedly received within the annular recess whereby the connector 50 is mounted removably to the receptacle 40 with the receptacle 40 as shown in FIG. 2. It will be understood that the tubular member 45 provided on the receptacle 40 and the tubular member 51 and cap 53 provided on the connector 50 comprise fittings for removably mounting the connector 50 to the receptacle 40.

Figure 7:
FIG. 7 is a vertical cross-sectional view taken generally along the line 7—7 in FIG. 2 in the direction of the arrows.
Figure 8:
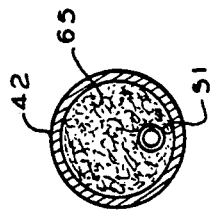
FIG. 8 is an elevational view of the filter shown in FIGS. 2 and 7 but with the filter shown separately.

It will be understood that before the connector 50 is mounted removably to the receptacle 40 a generally annular porous filter 65 shown in FIG. 8 is positioned in the internal cavity 47 of the receptacle 40 as shown in FIG. 1; to secure the filter 65 in the position shown in FIG. 2, it will be understood that the filter, or at least a portion thereof, may be wedged between the interconnection between the end cap 44 and the body portion 42 of the receptacle 40. As shown in FIG. 8, the filter 65 is provided with an internal opening 67 which is provided with a diameter permitting the ready passage therethrough of the tubular member 51 of the connector 50 upon the connector 50 being mounted to the receptacle 40 as described above. After such mounting, it will be understood that the filter 65, body 42 of receptacle 40 and the tubular member 51 of the connector 50 occupy the relative positions shown in FIG. 7.

Figure 6:
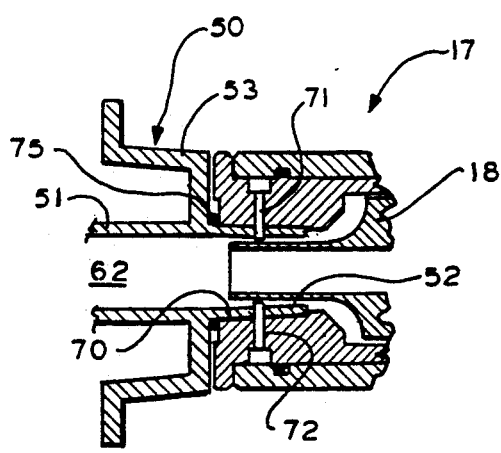
FIG. 6 is a partial vertical cross-sectional view showing in detail the manner in which the connector of FIGS. 2 and 4 is mounted removably to the handpiece shown in FIG. 1.

It will be further generally understood that the connector 50 is mounted removably to the leftward end of the handpiece 17 of the ultrasonic apparatus 30 as viewed in FIG. 2; mounting of the connector 50 to the handpiece 17 in turn mounts the receptacle 40 removably to the handpiece 17. As shown in FIG. 6, the leftward end of the handpiece 17 is provided with an inwardly extending tubular recess 70 into which a pair of opposed pins 71 and 72 extend inwardly. To mount the connector 50 to the handpiece 17, and referring again to FIG. 6, the opposed slots 55 and 56 formed in the tubular member 52 of the connector 50 are aligned with the opposed pins 71 and 72 and the tubular member 52 is inserted into the tubular recess 40 with the opposed pins 71 and 72 being received slidably in the inwardly extending portions 57 and 59 of the slots 55 and 56. Upon the tubular member 52 of the connector 50 being inserted into the tubular recess 70, the connector 50 is rotated with respect to the handpiece 17 to cause the opposed pins 71 and 72 to be received within the upwardly and downwardly extending portions 58 and 60 of the slots 55 and 56. This mounts the connector 50 removably to the handpiece 17 which in turn mounts the receptacle 40 removably to the handpiece 17. An "O-ring may be provided as shown in FIG. 6, intermediate the end cap 53 of the connector 50 and the leftward end of the handpiece 17 which is compressed upon the mounting of the connector 50 to the handpiece 17 to provide a fluid seal between the end of the ultrasonic conductor 18 and the atmosphere at the interconnection between the connector 50 and the handpiece 17. It will be understood that the tubular member 52 and the rearward portion of the handpiece 17 providing the inwardly extending tubular recess 70 comprise fittings for removably mounting the connector 50 to the handpiece 17. Further, it will be understood that the slots 55 and 56 formed in the tubular member 52 provided on the connector 50 and the inwardly extending opposed pins 71 and 72 extending into the tubular recess 70 comprise cooperative engaging means for providing the connection between the fittings comprised of the tubular member 52 of the connector 50 and the rearward portion of the handpiece 27 providing the inwardly extending tubular recess 70.

In operation, and referring again to FIG. 2, the ultrasonic apparatus 30 is connected to the ultrasonic generator 21 by the transducer power cable 12 and the receptacle 40 is connected to the vacuum source 23 by the flexible tube 11, through the canister 14 and the flexible tubing 24. The ultrasonic apparatus 30 is operated as described above with regard to the apparatus shown in FIG. 1 to successively remove, for example, the bone cement 2 of FIG. 1 by successively inserting cores of the bone cement into the ultrasonically vibrating tubular tip 6 of the electronic apparatus 30. As each successive core is inserted into the tip 6, the vacuum present in the receptacle 40 draws or aspirates the cores of bone cement from the tubular tip 6, through the ultrasonic conductor 18, through the passageway 62 provided in the connector 50 (FIG. 5) and into the cavity 47 provided in the receptacle 40 as shown in FIG. 2. It will be understood that in such drawing or aspiration of the bone cement cores 26 through the ultrasonic conductor 18, the passageway 62 provided in the connector 50 and into the cavity 47 of the receptacle 40, the removed bone cement cores 26 are provided with a linear path thereby substantially eliminating any possibility of the removed cement bone cores 26 from becoming jammed or lodged along the path of bone cement core removal. It will be further understood that this linear path is provided while a surgeon is grasping the handpiece 17, maneuvering the handpiece and ultrasonic apparatus 30 about and placing the handpiece 17 in different orientations with respect to the femur 1 of FIG. 1 to remove successive cores of the bone cement 2 thereby ultimately entirely, or at least substantially entirely, excavating the bone cement 2 from the femur 1. Referring still to FIG. 2 and to the operation of the apparatus of the present invention, it will be understood that the filter 65 residing in the internal cavity 47 of the receptacle 40 is positioned intermediate the internal cavity 47 and the passageway 49 formed in the fitting 48 whereby the bone cement cores 26 are prevented from being drawn or aspirated out of the internal cavity and into the flexible tubing 11 where such bone cement cores 26 could provide a blockage of the type noted above. The filter 65 may be made of a suitable porous material, such as a wire mesh, wherein the openings are sufficiently large to permit the required vacuum for drawing or aspirating the bone cement cores 26 through the acoustical inductor 18 and connector 50 into the receptacle 40 but such openings are sufficiently small to prevent the bone cement cores 26 from passing therethrough and escaping into the flexible tubing 11.

Figure 9:
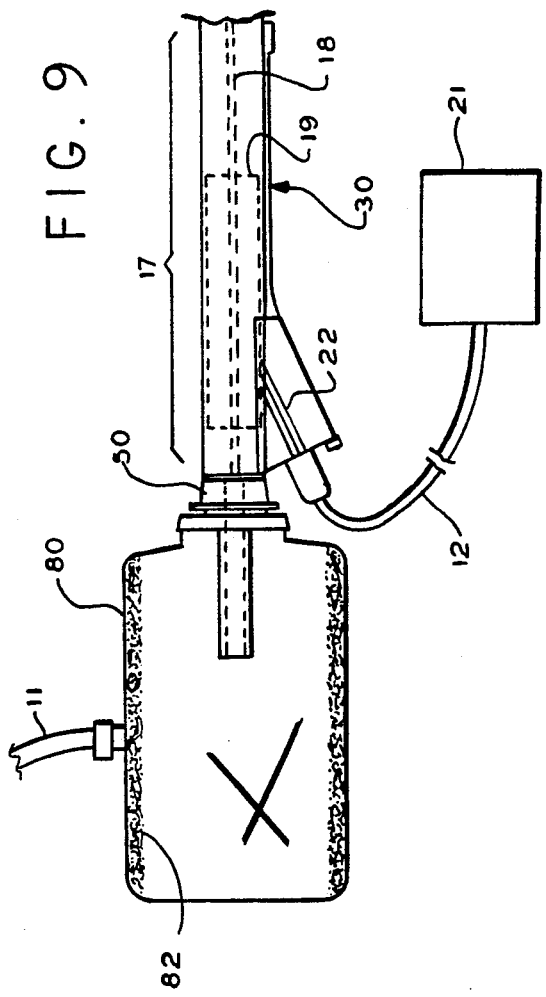
FIG. 9 is a partial view showing a side view of an alternate embodiment of a receptacle and filter of the present invention.

Referring now to FIG. 9, an alternate embodiment of receptacle filter of the present invention is shown. In this embodiment, the receptacle 80 is general cylindrical in configuration as is the filter 82 which is complementary in shape to the interior of the receptacle. Otherwise, the receptacle 80 and filter 82 function substantially the same as the receptacle 40 and filter 65 shown in FIG. 2.

It will be further understood that the apparatus of the present invention in addition to removing cores of thermoplastic material also may be used to remove cores of elastomeric material.

It will be understood that many variations and modifications may be made in the present invention without departing from the spirit and the scope thereof.

What is claimed is:

1. Apparatus for removing cores of thermoplastic and elastomeric material, comprising:
   a hand piece provided with a longitudinally extending tube of acoustically conductive material and an ultrasonic transducer acoustically coupled to said tube for causing said tube to vibrate at an ultrasonic frequency whereby upon engagement of at least an end portion of said tube with said material, cores thereof are removed and inserted into said tube; and
   receptacle means mounted on said handpiece in linear alignment with said tube and in fluid communication with said tube, and said receptacle means for being connected to a vacuum source to cause said cores inserted into said tube to be aspirated along a substantially linear path through said tube and into said receptacle means.

2. Apparatus according to claim 1 wherein said receptacle means is provided with filter means for preventing said cores from being aspirated out of said receptacle means.

3. Apparatus according to claim 1 wherein said apparatus further comprises connecting means for mounting said receptacle means removably on said handpiece, said connecting means having a fluid passageway extending therethrough for placing said receptacle means in said fluid communication with said tube.

4. Apparatus according to claim 3 wherein said receptacle means is provided with first fitting means, wherein said connecting means is provided with second and third fitting means and wherein said second fitting means are for interconnecting with said first fitting means to mount said connecting means removably to said receptacle means, wherein said handpiece is provided with fourth fitting means for interconnecting with said third fitting means to mount said connecting means removably to said handpiece and thereby to mount said receptacle means removably to said handpiece.

5. Apparatus according to claim 4 wherein said apparatus further comprises sealing means providing a fluid seal between said tube and the atmosphere at the interconnection of said third and fourth fitting means.

6. Apparatus for removing cores of thermoplastic and elastomeric material, comprising:
 a handpiece provided with a longitudinally extending tubular ultrasonic conductor of acoustically conductive material, said ultrasonic conductor having first and second ends;
 a tubular tip of acoustically conductive material mounted removably to said first end of said ultrasonic conductor;
 an ultrasonic transducer mounted on said handpiece and acoustically coupled to said ultrasonic conductor and for causing said ultrasonic conductor and said tubular tip to vibrate at an ultrasonic frequency whereby upon engagement of said tubular tip with said material, cores thereof are removed and inserted into said tubular tip;
 receptacle means;
 connecting means for removably mounting said receptacle means to said second end of said handpiece and for placing said receptacle means in linear alignment and in fluid communication with said tubular ultrasonic conductor and said tubular tip; and
 said receptacle means for being connected to a vacuum source to cause said cores inserted into said tubular tip to be aspirated along a linear path extending from said tubular tip through said ultrasonic conductor and said connecting means and directly into said receptacle means.

7. Apparatus according to claim 6 wherein said receptacle means is provided with filter means positioned intermediate said vacuum source and said ultrasonic conductor to prevent said cores from being aspirated out of said receptacle means.

8. Apparatus according to claim 6 wherein said receptacle means is provided with an opening through which said receptacle means is connected to said vacuum source by a flexible tube capable of assuming a curvature which can substantially prevent the passage therethrough of said cores, wherein said receptacle provides an internal cavity for receiving said cores, and wherein said receptacle means is provided with filter means residing in said cavity and covering said opening to prevent said cores from being aspirated out of said cavity through said opening and into said flexible tube.

9. Apparatus according to claim 8 wherein said receptacle means is provided with an outwardly extending first tubular member comprising first fitting means, wherein said connecting means is provided with an outwardly extending second tubular member and with a radially outwardly extending cap providing in combination with said second tubular member an annular recess, said second tubular member and said cap comprising second fitting means, said second tubular member for being inserted into said first tubular member with a portion of said second tubular member extending into said cavity and said annular recess for wedgedly receiving said first tubular member to removably interconnect said first and second fitting means, wherein said filter means are generally annular filter means including an opening through which said portion of said second tubular member extending into said cavity extends to mount said filter on said portion of said second tubular member and internally of said cavity.

10. Apparatus according to claim 8 wherein said filter means are generally cylindrical filter means, wherein said receptacle includes an inner wall generally providing said cavity with a cylindrical shape and wherein said cylindrical filter means are generally complementary in shape to said inner wall to cause said cylindrical filter means to cover said opening through which said receptacle means is connected to said vacuum source.

11. Apparatus according to claim 6 wherein said receptacle means is provided with first fitting means, wherein said connecting means is provided with second and third fitting means and wherein said first and second fitting means are for being interconnected to mount said connecting means removably to said receptacle means, wherein said handpiece is provided with fourth fitting means and wherein said third and fourth fitting means are for being interconnected to mount said connecting means removably to said handpiece and thereby to mount said receptacle means removably to said handpiece.

12. Apparatus according to claim 11 wherein said receptacle means is provided with an outwardly extending first tubular member comprising said first fitting means, wherein said connecting means is provided with an outwardly extending second tubular member and with a radially outwardly extending cap providing in combination with said second tubular member an annular recess, said second tubular member and said cap comprising said second fitting means, said second tubular member for being inserted into said first tubular member and said annular recess for wedgedly receiving said first tubular member to provide said interconnection between said first and second fitting means.

13. Apparatus according to claim 12 wherein said connecting means is provided with an outwardly extending third tubular member comprising said third fitting means, wherein said handpiece is provided with an inwardly extending tubular recess comprising said fourth fitting means, wherein said third tubular member and said tubular recess are provided with cooperative engaging means for providing said connection between said third and fourth fitting means, and said second and third tubular members cooperatively providing a fluid passageway for placing said receptacle means in said fluid communication with said ultrasonic conductor.

14. Apparatus according to claim 13 wherein said cooperative engaging means comprise a pair of opposed slots formed in said third tubular member, one of said slots including an inwardly extending portion and an upwardly extending portion provided at the inward end of said inwardly extending portion, the other of said slots including an inwardly extending portion and a downwardly extending portion provided at the inward end of said inwardly extending portion, and wherein said cooperative engaging means further comprise a pair of outwardly extending opposed pins provided in said tubular recess, said tubular recess for slidably and rotatably receiving said third tubular member upon said third tubular member being inserted into said tubular recess, said pins for being received in said inwardly extending portions of said slots and upon relative rotational movement between said third tubular member and said handpiece, said pins for being received within said upwardly and downwardly extending portions of said slots to removably mount said connecting means to said handpiece.

15. Apparatus according to claim 13 wherein said connecting means further comprise an O-ring for surrounding said third tubular member and upon said connecting means being mounted to said handpiece said O-ring for being compressed to provide a fluid seal between said ultrasonic conductor and the atmosphere at said interconnection between said third and fourth connecting means.

16. Apparatus for receiving cores of thermoplastic and elastomeric material removed from a body of said material by ultrasonic apparatus using ultrasonic energy applied to a tubular ultrasonic conductor extending through the apparatus, upon removal said cores residing in said apparatus, comprising: receptacle means mountable on said ultrasonic apparatus and in linear alignment with said tubular ultrasonic conductor, said receptacle means provided with a cavity for receiving said cores and said receptacle means for being connected to a vacuum source to aspirate said cores from said ultrasonic apparatus and into said cavity.

17. Apparatus according to claim 16 wherein said receptacle means further includes filter means residing in said cavity and for providing a filter between said vacuum source and said cavity to prevent said cores of material from being aspirated out of said cavity.

18. Apparatus according to claim 16 wherein said receptacle means comprise a generally cylindrical transparent plastic canister which permits the quantity of cores accumulated in said transparent canister to be viewed by the human eye.

19. Apparatus for removably mounting a receptacle apparatus to an ultrasonic apparatus comprising:
connecting means and receptacle means, said connecting means including means for removably mounting said receptacle means directly to the ultrasonic apparatus and in linear alignment with a tubular ultrasonic conductor extending through said ultrasonic apparatus and through which removed cores of thermoplastic and elastomeric material pass;
said connecting means also including means for placing said receptacle means in fluid communication with said conductor; and
said receptacle means including means for being connected to a vacuum source to aspirate said cores from said ultrasonic apparatus, through said connecting means and into said receptacle means.

20. Apparatus according to claim 19 wherein said receptacle means is provided with a cavity for receiving said cores and wherein said receptacle means are provided with filter means residing in said cavity and said filter means for preventing cores received within said cavity from being aspirated out of said cavity.

21. Apparatus according to claim 18 wherein said receptacle means is provided with first fitting means, wherein said connecting means is provided with second and third fitting means and wherein said first and second fitting means are for being interconnected to mount said connecting means removably to said receptacle means, wherein said ultrasonic apparatus is provided with fourth fitting means and wherein said third and fourth connecting means are for being interconnected to mount said receptacle means removably to said ultrasonic apparatus and thereby to mount said receptacle means removably to said ultrasonic apparatus.

22. Apparatus according to claim 21 wherein said receptacle means is provided with an outwardly extending first tubular member comprising said first fitting means, wherein said connecting means is provided with an outwardly extending second tubular member and with a radially outwardly extending cap providing in combination with said second tubular member an annular recess, said second tubular member and said cap comprising said second fitting means, said second tubular member for being inserted into said first tubular member and said annular recess for wedgedly receiving said first tubular member to provide said interconnection between said first and second fitting means.

23. Apparatus according to claim 21 wherein said connecting means is provided with an outwardly extending third tubular member comprising said third fitting means, wherein said ultrasonic apparatus is provided with an inwardly extending tubular recess comprising said fourth fitting means, wherein said third tubular member and said tubular recess are provided with cooperative engaging means for providing said connection between said third and fourth fitting means, and said second and third tubular members cooperatively providing a fluid passageway for placing said receptacle means in said fluid communication with said ultrasonic conductor.

24. Apparatus according to claim 22 wherein said cooperative engaging means comprise a pair of opposed slots formed in said third tubular member, one of said slots including an inwardly extending portion and an upwardly extending portion provided at the inward end of said inwardly extending portion, the other of said slots including an inwardly extending portion and a downwardly extending portion provided at the inward end of said inwardly extending portion, and wherein said cooperative engaging means further comprise a pair of outwardly extending opposed pins provided in said tubular recess, said tubular recess for slidably and rotatably receiving said third tubular member and upon said third tubular member being inserted into said tubular recess said pins for being received in said inwardly extending portions of said slots and upon relative rotational movement between said third tubular member and said handpiece, said pins for being received within said upwardly and downwardly extending portions of said slots to removably mount said connecting means to said handpiece.

25. Apparatus according to claim 24 wherein said connecting means further comprise an O-ring for surrounding said third tubular member and upon said connecting means being mounted to said ultrasonic apparatus said O-ring for being compressed to provide a fluid seal between said ultrasonic conductor and the atmosphere at said interconnection between said third and fourth connecting means.

* * * * *